United States Patent [19]

Baker et al.

[11] Patent Number: 5,342,760
[45] Date of Patent: Aug. 30, 1994

[54] DETERMINATION OF ESTRADIOL BY COMPETITIVE IMMUNOASSAY

[75] Inventors: Harold N. Baker; Katherine K. Eng, both of Libertyville; William D. Gurner, Chicago; Michael K. Massei, Lake Villa; Necklaws: Elizabeth C., Grayslake; Eugene W. Osikowicz, Lake Zurich; Sally K. Ramp; Paula Trach, both of Gurnee, all of Ill.

[73] Assignee: Abbott Laboratories, Abbott Park, Ill.

[21] Appl. No.: 896,269

[22] Filed: Jun. 10, 1992

[51] Int. Cl.$^5$ ............... G01N 33/547; G01N 33/548
[52] U.S. Cl. ..................... 435/7.92; 435/7.72; 435/962; 436/526; 436/530; 436/533; 436/544; 436/546; 436/817; 436/825
[58] Field of Search ............ 435/7.93, 188, 7.72, 435/962, 544; 436/533, 546, 526, 530, 817, 825

[56] References Cited

U.S. PATENT DOCUMENTS

| | | | |
|---|---|---|---|
| 4,097,586 | 6/1978 | Gross | 436/543 |
| 4,275,149 | 6/1981 | Litman et al. | 435/7 |
| 4,477,577 | 10/1984 | Nakamura et al. | 436/510 |
| 4,857,652 | 8/1989 | Schaap | 549/510 |
| 4,931,223 | 6/1990 | Bronstein et al. | 252/700 |
| 4,931,569 | 6/1990 | Edwards et al. | 549/221 |
| 4,962,192 | 10/1990 | Schaap | 536/18.1 |
| 4,978,614 | 12/1990 | Bronstein | 435/21 |

FOREIGN PATENT DOCUMENTS

| | | | |
|---|---|---|---|
| 383313 | 8/1990 | European Pat. Off. | 435/7.93 |
| 9101492 | 2/1991 | PCT Int'l Appl. | |

OTHER PUBLICATIONS

B. Desfosses et al., J. Steroid Biochem., vol. 19, No. 6, 1811–1816 (1983).
T. Nambara et al., J. Steroid Biochem., vol. 20, No. 2, 621–626 (1984).
Philip et al., "Relative Binding of Certain Steroids of Low Polarity to Human Sex Hormone—Binding Globulin: Strong Binding of 2-Methoxyestrone, a Steroid Lacking the 17 β-OH Group," *Steroids*, 47:373–379, Jun., 1986.
Philip et al., "Low Polarity Ligands of Sex Hormone-Binding Globulin in Pregnancy. Part I-Characterization," *J. Steroid Biochem.*, 32:865–872, 1989.
Fiore et al., "The Abbott IMx TM Automated Benchtop Immunochemistry Analyzer System," *Clin. Chem.*, 34/9:1726–1732, 1988.
Dawson et al., "A Simple and Effecient Method for Raising Steroid Antibodies in Rabbits," *Steroids*, 31:357–366, Mar., 1978.
Pandey et al., "Enzyme Immunosorbant Assay of Oestradiol in Unextracted Plasma Using Penicillinase as Label," *Clinica Chimica Acta*, 190:175–184, 1990.
Maurel et al., "A Highly Sensitive Microtitre Plate Enzyme Immunoassay for Oestradiol-17β," *J. Immunolog. Methods*, 102:165–172, 1987.
De Boever et al., "Direct Chemiluminescence Immunoassay for Estradiol in Serum," *Clin. Chem.*, 32:1895–1900, 1986.
Roda et al., "Development of a Sensitive, Direct Luminescent Enzyme Immunoassay for Plasma Estradiol-17β," *Anal. Biochem.*, 156:267–273, 1986.
De Lauzon et al., "Improvement of Estradiol Enzymoimmunoassay, Using a Monoclonal Antibody and an Avidin/Biotin Amplification System,"*J. Immunoassay*, 10:339–357, 1989.

*Primary Examiner*—Mary E. Ceperley
*Attorney, Agent, or Firm*—Wean Khing Wong

[57] ABSTRACT

The present invention relates to the measurement of estradiol using competitive immunoassay methods. The inventors unexpectedly discovered that estrone and its derivatives conjugated to a label is a particularly effective tracer when used in conjunction with estradiol specific antibodies to determine estradiol levels in fluid samples. The present invention also utilizes 5α-dihydrotestosterone to enhance the assay performance.

11 Claims, No Drawings

DETERMINATION OF ESTRADIOL BY COMPETITIVE IMMUNOASSAY

BACKGROUND OF THE INVENTION

Estradiol (1,3,5(10)-Estratrien-3,17a-diol) is secreted by the ovary and placenta. It is synthesized by the aromatization of androgens in the thecal and granulosa cells of the ovary and placenta. The aromatization is stimulated by follitropin (FSH). Estradiol synthesis in turn stimulates production of Lutropin (LH) receptors necessary for the synthesis of androgen precursors.

Estradiol is important for female sexual differentiation during gestation, sexual development at the onset of puberty, and regulation of the menstrual cycle. The menstrual cycle is the result of a precise coordination of the functional characteristics of the Central Nervous System, the hypothalamus, the pituitary, the ovary, and the endometrium which regulate the cyclic release of Gonadotropin Releasing Hormone (GnRH), LH and FSH, and ovarian steroids (Estradiol and Progesterone). Estradiol is involved in both the stimulation and inhibition of the release of the gonadotropins, exerting both a positive and a negative feedback. Early in the follicular phase, ovarian secretion of estradiol from the thecal and granulosa cells is modest. During the follicular phase, estradiol stimulates endometrial growth (repairing the endometrium after menses). Toward mid-cycle, LH production increases and results in the release of the ovum by the rupture of the developed follicle. After ovulation, estradiol secretion declines slightly. During the luteal phase, estradiol along with progesterone are secreted by the corpus luteum stimulating further endometrial growth. If the ovum is not fertilized, there is a further drop in estradiol and progesterone. This drop in estradiol and progesterone initiates menses.

The measurement of estradiol is important for the evaluation of normal sexual development (menarche), causes of infertility (anovulation, amenorrhea, dysmenorrhea), and menopause. Normal estradiol levels are lowest at menses and during the early follicular phase (25–75 pg/ml). The levels rise in the late follicular phase to a peak of 200–600 pg/mL just before the LH surge initiates ovulation. As LH peaks, estradiol begins to decrease before rising again during the luteal phase (100–300 pg/mL). If conception does not take place, estradiol falls further to its lowest levels, thus initiating menses. If conception occurs, estradiol levels continue to rise, reaching levels of 1–5 ng/ml during the first trimester, 5–15 ng/ml during the second trimester, and 10–40 ng/ml during the third trimester. During menopause, estradiol levels remain low.

There are various methods for measuring estradial levels in serum. However, each of these methods utilize radioactive elements as labels and suffer from several disadvantages. The methods require several different steps including manual steps, several vessels, and are either nonautomated or only semiautomated. Radiolabels are problematic because the expense involved in such assays are much greater than in non-radiolabeled assay formats. For example, more highly skilled laboratory personnel are required and waste disposal is more tightly controlled and regulated. The following are commercially available radioimmunoassay methods for determining estradiol level in serum samples.

One assay for estradiol (commercially available from Pantex) is a direct, non-extraction competitive assay. Radiolabeled estradiol tracer, anti-estradiol antibody and sample are mixed and incubated for two hours. Anti-antibody antibody is added and the mixture is incubated for 15 minutes to form a precipitate. The mixture is centrifuged to pellet the precipitate formed. The supernatant is decanted and the radioactivity of the precipitant is measured. The radioactivity measured is compared to a radioactivity vs. estradiol concentration plot to determine the estradiol concentration in the sample. The following compounds are known to cross-react in the assay: $\alpha$-Estradiol (1.4%) and Danazol (0.6%).

Another assay for estradiol (Coat-A-Count Radioimmunoassay (RIA) for Estradiol commercially available from Diagnostic Products Corporation) is a direct, non-extraction antibody coated tube competitive assay. Each tube is coated with anti-estradiol antibody. Radiolabeled estradiol tracer and sample are incubated in the tube for three (3) hours. After decanting the mixture and washing the tube, the radioactivity of the tube is measured. The radioactivity measured is compared to a radioactivity vs. estradiol concentration plot to determine the estradiol concentration in the sample. The following compounds are known to cross-react in the assay: Ethinyl Estradiol (1.8%); Estrone (1.1%); Estradiol-3$\beta$-D-glucuronide (0.7%); Estradiol-3-Sulfate (0.3%); and 19-Nortestosterone (0.25%).

Yet another assay for estradiol (Estradiol MAIA commercially available from Serono) is also a direct, non-extraction competitive assay. Radiolabeled estradiol tracer, anti-estradiol antibody and the sample are incubated for one to three hours (depending on the assay sensitivity and precision desired) to permit the formation of antibody-estradiol complexes. The complexes are separated from the sample by incubation of the reaction mixture with anti-antibody antibody coated magnetic particles followed by sedimentation of the magnetic particles through the application of a magnetic field. The separated particles are then washed. The measured radioactivity level of the particles is compared to a radioactivity vs. estradiol concentration plot to determine the estradiol concentration in the sample. The following compounds are known to cross-react in the assay: Estrone (2.6%); EstradioI-Dipropionate (0.3%); Estradiol-3$\beta$-D-glucuronide (0.2%); and Estriol (0.2%).

Some non-radiolabeled immunoassays have been reported, but do not have the sensitivity or specificity needed to accurately and precisely measure estradiol levels. Dawson et al. (Steroids, 31:357–366, 1978) tested rabbit polyclonal anti-estradiol antibodies using horseradish peroxidase coupled to estrone at carbon 11. The cross-reactivities of the antibodies to estrone ranged from 5% to 120%. Such cross-reactivities would not be acceptable in an estradiol specific assay. Thus, an enzyme immunoassay that utilizes a conjugate where the enzyme is coupled to position 11 of estrone would not likely produce a satisfactory assay.

Pandey et al. (Clinica Chimica Acta, 190:175–184, 1990) reported an enzyme-linked immunosorbant assay (ELISA) using the conjugate estradiol-6-(O-carboxymethyl)oxime linked to penicillinase with anti-estradiol antibody coated wells of a microtiter plate. The assay had a lower sensitivity limit of 25 pg/mL, but required a two (2) hour incubation of the reaction mixture at 37° C. and after washing, the enzyme substrate/enzyme reaction required incubation at 37° C. for one (1) hour. Thus the overall assay time was in excess of three (3) hours. Maurel et al. (J. Immunolog. Methods, 102:165-172, 1987) also reported an ELISA using an estradiol-6-(O-carboxymethyl)oxime conjugated to β-galactosidase, which had improved sensitivity over Pandey et al.'s assay. However, as in Pandey et al.'s method, Maurel et al.'s method requires extensive incubation times. The anti-estradiol antibody coated on microtiter wells are incubated with the sample for ninety (90) minutes at 37° C., then incubated with conjugate for ninety (90) minutes, and then after washing the enzyme activity was determined after two (2) hours at 42° C. Thus, the assay time was well in excess of three (3) hours.

De Boever et al. (Clin. Chem., 32:1895-1900, 1986) reported a chemiluminescence immunoassay for estradiol with a sensitivity limit of about 49 pg/mL and an assay time of in excess of ninety (90) minutes. Roda et al. (Anal. Biochem., 156:267-273, 1986) reported a luminescent enzyme immunoassay for estradiol which required over four (4) hours to perform.

De Lauzon et al. (J. Immunoassay, 10:339-357, 1989) reported a competitive enzyme immunoassay for estradiol using microtiter plate wells coated with estradiol coupled to bovine serum albumin (BSA). The sample and peroxidase labeled anti-estradiol antibody were incubated in the wells for two (2) hours at room temperature. Alternatively, biotinylated anti-estradiol antibodies were utilized followed by a second incubation of three (3) hours with avidin coupled to peroxidase.

Clearly, there is a need for an estradiol non-radiolabel immunoassay that is rapid, accurate, sensitive, easy to perform, free from interferences and relatively insensitive to experimental variables such as pH and temperature. An object of the present invention is to develop an assay method and reagents to perform estradiol measurements accurately and with precision without the need of a radiolabeled tracer. Because of the very low concentrations of estradiol present in biological fluid samples (0.025-40 ng/mL), any alternative method must be very sensitive. The existing methods utilize long incubation times to overcome this sensitivity requirement. Another object of this invention is to eliminate the long incubation times required in non-radiolabeled immunoassays.

SUMMARY OF THE INVENTION

The present invention relates to the measurement of estradiol using competitive enzyme immunoassay methods involving the use of estrone conjugated to a label at the 6 position. The inventors unexpectedly discovered that estrone and its derivatives conjugated to a label at the 6 position may be used in conjunction with estradiol specific antibodies to determine estradiol levels in fluid samples. The present invention also utilizes 5α-dihydrotestosterone to enhance the assay performance.

DETAILED DESCRIPTION OF THE INVENTION

The present invention relates to methods and reagents useful in the measurement of estradiol in fluid samples. The inventors unexpectedly discovered that estrone and its derivatives conjugated to a label can be used in conjunction with estradiol specific binding members to measure estradiol levels in fluid samples, such as blood, plasma, whole blood, cerebral spinal fluid, saliva, urine, and the like. The present invention uniquely involves the measurement of estradiol concentrations in fluid samples using such estrone label conjugates. In addition, estradiol is known to bind to Sex Hormone Binding Globulin (SHBG) (Philip et al., Steroids, 47:373-379, 1986) which is present in fluid samples, such as serum, plasma, whole blood and the like. In order to measure the total estradiol in a sample containing SHBG, the estradiol bound to SHBG must be released. The inventors discovered that the use of a buffered solution of 5α-dihydrotestosterone will release substantially all of the estradiol bound to SHBG.

Testosterone (Philip et al., J. Steroid Biochem., 32:865-872, 1989) and its derivatives are known to displace estradiol from SHBG at pH 8.0 (De Boever et al., Clin. Chem., 32:1895-1900, 1986). As De Boever et al. reported and the inventors observed, not all of the estradiol is substantially displaced from SHBG at pH 7.5-8.0 by 5-dihydrotestosterone. Substantially all of the the the estradiol is displaced from SHBG by 5α-dihydrotestosterone at a concentration within the range of about 1 μg/mL to about 5 μg/mL, preferably within the range of about 1 μg/mL to about 3 μg/mL most preferably at a concentration of about 2 μg/mL, at a pH within the range of about 4.5 to about 6.7, preferably within the range of about 5.0 to about 6.0, most preferably at a pH of about 5.7. Preferably, the buffer is a combination of glycine at a concentration within the range of about 0.25M to about 1M, more preferably within the range of about 0.4M to about 0.6M, and citric acid at a concentration within the range of about 0.2M to about 0.5M, more preferably within the range of about 0.2M to about 0.3M, though other buffers or buffer combinations which are capable of buffering a solution within the above effective reaction range are acceptable. The buffer also preferably contains saponin at a concentration of at least about 0.5% (w/v), more preferably within the range of about 0.5% (w/v) to about 1.25% (w/v), and most preferably at a concentration of about 0.75% (w/v). The presence of red blood cells in a serum sample tended to cause the measured estradiol levels to be elevated. The addition of saponin substantially reduced the effect of the red blood cells.

Specific binding members specific for estradiol include estradiol specific binding proteins, such as monoclonal and polyclonal antibodies and other estradiol specific synthetic or recombinant proteins that specifically bind lipoprotein cholesterol particles. For example, it is well known by those skilled in the art that monoclonal and polyclonal antibodies can be produced that specifically bind to steroids such as estradiol. When an immunogen comprising estradiol or a derivative of estradiol coupled, typically through a covalent bond, to a carrier protein, such as albumin and the like, is injected into an animal, the animal's immune system will produce polyclonal antibodies that specifically bind to estradiol. General methods for the preparation of monoclonal antibodies to analytes using mice or rats are well known to those skilled in the art. More recently the preparation of analyte specific synthetic and recombinant proteins have been reported and the same methods can be readily adapted to the preparation of estradiol specific binding synthetic and recombinant proteins useful in this invention.

The inventors discovered that a compound, estrone, which has a reported very low cross-reactivity (less than 5% and in some cases less than 1% cross-reactivity) with estradiol specific antibody, surprisingly acts as an exceptional labeled reagent for detecting exceedingly low levels of estradiol in a very rapid assay format. The term "conjugate", as used herein, refers to any substance comprising estrone or a derivative of estrone coupled to a label. The coupling is preferably covalent. A preferred conjugate for use in this invention comprises

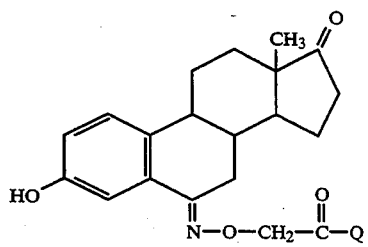

wherein Q is a label.

The term "label", as used herein, refers to any substance which can be attached to estrone or its derivatives and which is capable of producing a signal that is detectable by visual or instrumental means. Various suitable labels for use in the present invention can include catalysts, enzymes, liposomes or other vesicles containing signal producing substances such as chromogens, catalysts, fluorescent compounds, chemiluminescent compounds, enzymes and enzyme substrates, and the like. A large number of enzymes suitable for use as labels are disclosed in U.S. Pat. No. 4,275,149 incorporated herein by reference. Such enzymes include glucosidases, galactosidases, phosphatases and peroxidases, such as alkaline phosphatase and horseradish peroxidase which are used in conjunction with enzyme substrates, such as fluorescein di(galactopyranoside), nitro blue tetrazolium, 3,5',5,5'-tetranitrobenzidine, 4-methoxy-1-naphthol, 4-chloro-1-naphthol, 4-methylumbelliferyl phosphate, 5-bromo-4-chloro-3-indolyl phosphate, chemiluminescent enzyme substrates such as the dioxetanes described in WO 88100694 and EP 0-254-051-A2 and derivatives and analogs thereof. Preferably, the label is an enzyme and most preferably the enzyme is alkaline phosphatase.

The conjugate is preferably prepared by coupling the label to the conjugate precursor (which is commercially available from Sigma Chemical Company)

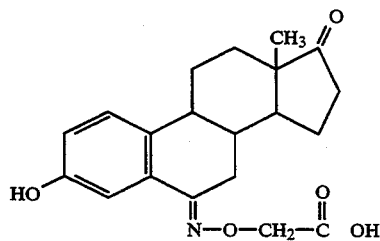

using a carbodiimide compound, such as 1,ethyl-3-(3-dimethylaminopropyl)carbodiimide, or by first forming an active ester, such as an N-hydroxysuccinimide active ester and then reacting the active ester with the label. Other coupling methods and conditions well known to those skilled in the art may also be used to prepare the conjugate.

Preferably, estradiol is measured according to the invention using a solid phase having a specific binding member specific for estradiol bound thereto. The solid phase and the sample are separated so that the amount of estrone enzyme conjugate bound to the solid phase or the amount of estrone enzyme conjugate remaining in solution can be determined. The amount of estrone enzyme conjugate on the solid phase or in solution can be correlated to the concentration of estradiol in the sample using a enzyme activity vs. estradiol concentration plot, typically referred to as a standard curve. A standard curve is prepared by performing the assay using calibrators such as those in Table 1 (below). Controls are used to verify that the curve is viable. When an sample with an unknown estradiol level is assayed, the measured assay signal is compared to the standard curve and the estradiol level corresponding to that signal is the estradiol level of the sample.

The specific binding member may be bound to the solid phase by physical or chemical means, preferably by means of a direct covalent bond. The specific binding member should be bound to the solid phase in such a way that substantially none of the specific binding members detach during the subsequent reactions and wash steps. Regardless of the specific binding member and the coupling method selected, the specific binding member must be able to bind to estradiol and the estrone enzyme conjugate after being coupled to the solid phase.

A solid phase according to the present invention may be a mixture of polymeric microparticles with chemically or physically bound specific binding members specific for estradiol. Microparticles that can be used include polystyrene, carboxylated polystyrene, polymethylacrylate or similar particles with a radius ranging from about 0.1 μm to about 0.25 inches. A preferred separation method for these particles is the use of microparticle capture on a porous matrix such as glass fiber (see below).

Other solid phases that can be used include a mixture of magnetizable polymeric microparticles with chemically or physically bound specific binding members specific for estradiol. Magnetizable microparticles that can be used preferably have ferric oxide or chromium oxide cores and a polystyrene, carboxylated polystyrene or polymethylacrylate coating. Yet other solid supports are known to those in the art and include the walls of wells of a reaction tray, tubes, polystyrene beads, nitrocellulose strips, membranes and the like. Natural, synthetic, or naturally occurring materials that are synthetically modified, can be used as a solid phase material including polysaccharides, e.g., cellulose materials such as paper and cellulose derivatives such as cellulose acetate and nitrocellulose; silica; inorganic materials such as deactivated alumina, diatomaceous earth, MgSO₄, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon); porous gels such as silica gel, agarose, dextran, and gelatin; polymeric films such as polyacrylamide; and the like. In any case, the solid phase material should have reasonable strength or strength can be provided by means of a support, and should not interfere with the production of a detectable signal.

An alternative preferred separation method is described in co-pending U.S. patent application Ser. Nos. 150,278, abandoned, filed Jan. 20, 1988 and 375,029, abandoned, filed Jul. 7, 1989 both of which enjoy common ownership and both of which are incorporated herein by reference. These applications describe the use of ion capture separation, in which the specific binding members used in the assay in question are chemically attached to a first polyionic compound and a porous matrix having bound thereto a second polyionic compound that binds to the first polyionic compound. A specific binding pair is formed and separated from the reaction mixture by an electrostatic interaction between the first and second polyionic compounds. A specific binding member of the specific binding pair is preferably covalently coupled to the first polyionic compound.

Preferably, the first polyionic compound is a polyanionic acid, such as polyaspartic acid, heparin, carboxymethyl amylose, polyglutamic acid or polyacrylic acid, and the second polyionic compound is a cationic polymer, such as GafQuat™ which is a polymeric quaternary ammonium compound (GAF Corporation, Wayne, N.J., 07470), diethylaminoethyl-dextran (Sigma Chemical Company, St. Louis, Mo.), water soluble cellulose derivatives such as Celquat™ L-200 and Celquat™ H-100 (National Starch & Chemical Corporation, Bridgewater, N.J., 08807) which are both polymeric quaternary compounds, or Merquat® 100 (commercially available from Calgon Corporation). The porous matrix is treated with the cationic polymer to render the matrix positively charged. The cationic polymer is bound to the matrix by absorption, adsorption, or covalent or ionic coupling. The separation of the reaction products is effected by the electrostatic interaction between the positively charged pad and the negatively charged polyanion complex.

A porous matrix for use in this invention can include any suitable porous material. By "porous" is meant that the material is one through which fluids can flow and can easily pass. In the present invention, the matrix can include a polypropylene, polyethylene, Teflon, fiberglass, cellulose, or nylon pad or other porous material well known to those skilled in the art for use in a pour and flow-through assay device having one or more layers containing one or more of the assay reagents.

Preferred porous materials include a porous fiberglass material, such as a "Whatman 934-AH" filter paper, which has a nominal thickness of 0.33 mm, or the disposable IMx® cartridge and TestPack™ (fiber matrix) devices of Abbott Laboratories (Abbott Park, Ill., 60064). The thickness of such material is not critical, and will be a matter of choice, largely based upon the properties of the sample or analyte being assayed, such as the fluidity of the test sample.

Some enzyme substrates are converted into fluorescent compounds, such as 4-methylumbelliferone, by the appropriate enzyme. The quantity or rate at which the fluorescent compounds are formed over time is an indication of the quantity of enzyme present in the reaction. When the enzyme is a label, the quantity of enzyme present is related to the quantity of estradiol present in the sample. Thus the measurement of fluorescence can be related back to the quantity of estradiol present in the sample. The fluorescence can be measured by any method known to the art. For example, a fluorescence spectrometer is desirable, although the fluorescence spectrum can be observed with a visual spectrometer or photographed with a spectrograph of high light-gathering power.

In a preferred embodiment, the fluorescence is detected using an IMx® (Abbott Laboratories, Inc.) automated bench top analyzer that contains an optical assembly which is a fluorometer that uses a mercury arc lamp as its light source. This instrument is described by Fiore et al (Clin. Chem., 34/9:1726–1732, 1988), the contents of which are incorporated herein by reference. The instrument utilizes an IMx® disposable cartridge (commercially available from Abbott Laboratories, Illinois) which contains a porous matrix to capture microparticles containing anti-estradiol antibodies which have been exposed to a conjugate and the sample. The label used in the conjugate is preferably alkaline phosphatase. The conjugate and the estradiol in the sample compete for available binding sites on the microparticles. The microparticles are separated from the sample and the quantity of conjugate present on the microparticles is determined from the rate at which 4-methylumbelliferyl phosphate is converted into 4-methylumbelliferone. From a standard curve of rate of 4-methylumbelliferone formation versus estradiol concentration, the quantity of estradiol in the sample can be determined.

The standard curve, also known as a calibration curve, of rate of 4-methylumbelliferone formation versus estradiol concentration is generally prepared from calibrator solutions containing known estradiol concentrations. Preferably; six calibrators are used to obtain a calibration curve, though more or less calibrators can be used depending on the accuracy and precision of the result desired. Preferably, the calibrators contain increasing amounts of estradiol. For example, Table 1 illustrates the composition of one set of calibrators (see Example 4). Controls are generally used in conjunction with an assay to confirm the viability of a calibration curve or assay reagents. Preferably, the formulation of the controls are the same as the calibrators with the exception that the estradiol concentration may not be identical with any one of the calibrators. For example, controls having an estradiol concentration of 150, 500 and 1125 pg/mL would be suitable controls for the calibrators in Table 1. One skilled in the art would be capable of devising other calibrator and control formulations.

TABLE 1

| Calibrator | Estradiol Concentration (pg/mL) |
|---|---|
| F | 3000 |
| E | 1500 |
| D | 750 |
| C | 250 |
| B | 50 |
| A | 0 |

To maintain aseptic conditions throughout the procedure, it may be desirable to add a small quantity of an antimicrobial agent to the system which may include solvents, antibiotics and poisons.

The following examples are illustrative of the invention and are in no way to be interpreted as limiting the scope of the invention, as defined in the claims. It will be appreciated that one skilled in the art can conceive of many other devices and methods of use to which the present inventive concepts can be applied.

EXAMPLE 1

The following assay format was performed on an IMx® disposable cartridge by an IMx® instrument (both commercially available from Abbott Laboratories, Illinois and described in EP-A-288 793 and in Fiore et al., Clin. Chem. 34/9:1726–1732, 1988, both of which are incorporated herein by reference). Seventy-five microliters (75 µL) Of a serum sample were mixed with 35 µL of 5α-dihydrotestosterone buffer (DHT Buffer: 2

µg of 5α-dihydrotestosterone and 0.75% (w/v) saponin per milliliter of 0.5 mM glycine and 0.25 mM citrate buffer at pH 4.5), 50 µL of rabbit anti-estradiol antibody coated microparticles as prepared in Example 2, and 90 µL of IMx ® Buffer (commercially available from Abbott Laboratories, Illinois). The mixture was incubated from about 27.5 minutes at 37° C. One-hundred seventy-five microliters(175 µL) of the mixture was transferred to the fiber matrix of an IMx ® disposable cartridge (the fiber matrix is in liquid communication with an absorbent pad). The particles were captured by the fiber matrix and the solution was absorbed by the absorbent pad. The particles were then washed with IMx ® Buffer. Sixty microliters (60 µL) of conjugate was added to the matrix, incubated for 12 seconds, and then the matrix was washed again with IMx ® Buffer. Sixty-five microliters (65 µL) of a 1.2 mM solution of 4-methylumbelliferyl phosphate in 0.1M 2-amino-2-methyl-1-propanol buffer at pH 9 was added to the matrix and the rate of 4-methylumbelliferone formation was measured by fluorescence reflectance. The fluorescence was measured with a fluorometer that uses a mercury arc lamp as its light source (as described by Fiore, M. et al., Clin. Chem 34/9:1726–1732, 1988, the contents of which are incorporated herein by reference). Using the calibrators of Table 1, this assay format on the IMx ® instrument was observed to have a mean sensitivity of 13.9±4.3 pg/mL.

EXAMPLE 2

Anti-estradiol coated microparticles were prepared as follows:
  a. Rabbit anti-estradiol polyclonal antibodies were prepared by injecting rabbits with estradiol 6(O-carboxymethyl)oxime coupled to bovine serum albumin (commercially available from Sigma Chemical Company, MO.)in Freund's complete adjuvant and boosting with Freund's incomplete adjuvant.
  b. Polyclonal antibodies were isolated from the rabbit serum following standard procedures for antibody precipitation with 35% ammonium sulfate.
  c. Enough latex microparticles (commercially available from Seradyne, Ind.) are measured to produce a final reaction concentration of 1% (w/v) solids were mixed with 50 mM 2-[N-morpholino]ethanesulfonic acid (MES) buffer at pH 4–5, antibody from step b was added to a concentration of 0.9 mg/mL, and then 1-ethyl-3-(3-dimethylaminopropyl) carbodiimide (EDAC) was added to a concentration of 0.5 mg/mL. The mixture was incubated for 30 minutes and then diluted in 0.1M Tris buffer at pH 7.4 containing 0.1% (w/v) Tween 20 and 0.1M sodium chloride. The particles were filtered and re-suspended to about 9 µg/mL antibody which is about 0.01% solids with 0.1M bis[2-hydroxyethyl]iminotris[hydroxymethyl] methane (Bis-Tris) at pH 6.5 containing 0.1M sodium chloride, 13.6% (w/v) sucrose and 0.2 mg/mL normal rabbit IgG.

EXAMPLE 3

Estrone 6(O-carboxymethyl)oxime alkaline phosphiatase conjugate was prepared as follows:
  a. Ten micrograms (10 µG) of estrone 6(O-carboxymethyl)oxime (commercially available from Sigma Chemical Company, MO.) and 10 µG of N-hydroxysuccinimide were dissolved in 100 µL dimethylformamide (anhydrous). Forty micrograms (40 µg) of EDAC was added.
  b. An aliquot of the mixture in step a was added to alkaline phosphatase in carbonate buffer at pH 8 so that the ration of estrone to phosphatase is 10:1. The resulting conjugate was purified on a G25 Sephadex column and the purified conjugate was diluted to a concentration of about 1–10 µg.mL in 0.1M Bis-Tris buffer at pH 6.5 containing 0.5M sodium chloride, 1% (w/v) casein, 1 mM magnesium chloride and 0.1 mM zinc chloride.

EXAMPLE 4

The calibrators listed in Table 1 were prepared as follows:
  a. Steroid stripped serum was prepared by raising the pH of serum to pH 11 with 6N sodium hydroxide and let the mixture stand for about 18 hours at 2°–8° C. The pH was then adjusted to a pH of about 7.4–8. Fifty grams (50 g) of activated charcoal was added per liter of serum and the mixture was stirred for 2 hours at room temperature. The charcoal was then filtered away from the steroid stripped serum.
  b. Enough estradiol was then added to aliquots of steroid stripped serum to make the final concentration of each calibrator listed in Table 1. Controls are prepared in the same manner.

EXAMPLE 5

To demonstrate the effectiveness of displacing estradiol bound to SHBG with 5α-dihydrotestosterone (DHT), estradiol was spiked into normal human serum samples and then the samples were assayed according to the format described in Example 1 hereof. Estradiol was added to normal human serum samples so that the estradiol level was increased by 300 pg/mL. Prior to assaying the spiked samples, an aliquot of each sample was treated with 5α-dihydrotestosterone at pH 5.7 and at pH 7.5. Table 2 lists a representative sampling of the samples tested. % Recovery was calculated as follows:

$$\text{Percent Recovery} = \frac{\text{Spiked Value} - \text{Nascent Value}}{300} \times 100.$$

Spiked Value is the measured estradiol concentration in the sample after the sample was spiked with estradiol. Nascent Value is the measured estradiol concentration in the sample before the sample was spiked with estradiol.

TABLE 2

| Sample | DHT at pH 5.7 | | | DHT at pH 7.5 | | |
|---|---|---|---|---|---|---|
| | Nascent | Spiked | %* | Nascent | Spiked | %* |
| 1 | 71 | 428 | 119 | 132 | 484 | 117 |
| 2 | 52 | 428 | 125 | 93 | 475 | 127 |
| 3 | 0 | 307 | 102 | 21 | 338 | 106 |
| 4 | 209 | 540 | 111 | 296 | 656 | 120 |
| 5 | 1455 | 1746 | 97 | 1845 | 1969 | 41 |
| 6 | 0 | 282 | 94 | 38 | 328 | 97 |
| 7 | 155 | 485 | 110 | 273 | 654 | 127 |
| 8 | 17 | 299 | 94 | 120 | 516 | 132 |
| 9 | 6 | 313 | 102 | 72 | 381 | 103 |

*Percent Recovery

EXAMPLE 6

Cross-reactivity studies were performed using the assay format described in Example 1 hereof. To steroid stripped serum prepared as in Example 4 hereof, potential cross-reacting steroids were added and the samples were assayed. Table 3 lists the steroids tested, the maximum concentration tested and the percent cross-reactivity observed.

TABLE 3

| Steroid | Concentration (ng.mL) | % Cross-Reactivity |
| --- | --- | --- |
| Aldosterone | 300 | 0 |
| Androstenedione | 30,000 | 0.0009 |
| Clomiphene Citrate | 300 | 0 |
| Corticosterone | 100,000 | 0 |
| Cortisol | 100,000 | 0 |
| Danazol | 100,000 | 0.0003 |
| 11-Deoxycortisol | 4,000 | 0 |
| DHEA-Sulfate | 5,000 | 0 |
| DHEA | 4,000 | 0 |
| 5-DHT | 30,000 | 0.0008 |
| Estrone | 100 | 0.30 |
| Estriol | 300 | 0.05 |
| Ethinyl Estradiol | 100 | 0.42 |
| Estradiol-3-Glucuronide | 10 | 2.40 |
| Extradiol-17-Sulfate | 300 | 0 |
| Progesterone | 100,000 | 0 |
| Testosterone | 100,000 | 0.0003 |

EXAMPLE 7

Using the assay format of Example 1 hereof and the Coat-A-Count Estradiol assay (commercially available from Diagnostic Products Corporation), 434 individual serum samples were assayed for estradiol and the estradiol levels as measured by each method were correlated as shown in Table 4.

TABLE 4

| Number of Samples | Estradiol Range (pg/mL) | Intercept | Slope | Correlation Coefficient |
| --- | --- | --- | --- | --- |
| 340 | 0–1500 | 34 | 1.16 | 0.97 |
| 434 | 0–6400 | 72 | 1.06 | 0.98 |

The invention also encompasses kits for the determination of estradiol in a fluid sample. The kits comprise a solid phase coupled to an antibody specific for estradiol; a conjugate of the formula

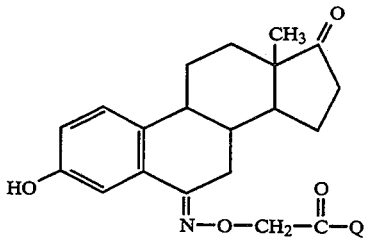

wherein Q is a label. Preferably, Q is an enzyme and the kit would further include an enzyme substrate. The kits can also include a sample pretreatment solution comprising 5α-dihydrotestosterone at a concentration within the range of about 1 μg/mL to about 5 μg/mL.

The embodiments described and the alternative embodiments presented are intended as examples rather than as limitations. Thus, the description of the invention is not intended to limit the invention to the particular embodiments disclosed, but it is intended to encompass all equivalents and subject matter within the spirit and scope of the invention as described above and as set forth in the following claims.

What is claimed is:

1. A method of determining the amount of estradiol in a blood sample comprising:
   a. incubating a mixture of a blood sample suspected of containing estradiol, a solid phase coupled to an antibody specific for estradiol, and a conjugate of the formula

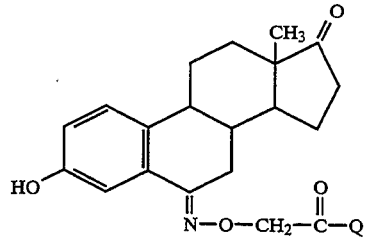

wherein Q is a label, to form estradiol/antibody complexes and conjugate/antibody complexes on said solid phase;
   b. separating said solid phase from said mixture;
   c. measuring the amount of label present in said mixture or on said solid phase; and
   d. determining the amount of estradiol in said sample from the amount of label.

2. The method of claim 1, wherein the label is selected from the group consisting of: catalysts, fluorescent compounds, chemiluminiscent compounds, enzymes, and enzyme substrates.

3. A kit for performing an estradiol competitive enzyme immunoassay comprising:
   a solid phase coupled to an antibody specific for estradiol and
   a conjugate of the formula

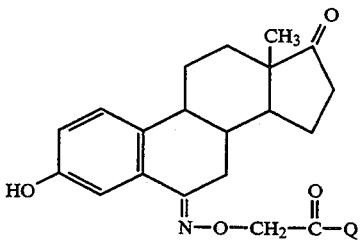

wherein Q is a label.

4. The kit of claim 3, wherein the label is selected from the group consisting of: catalysts, fluorescent compounds, chemiluminiscent compounds, enzymes, and enzyme substrates.

5. A method of determining the amount of estradiol in a blood sample comprising:
   a. incubating a mixture of a blood sample suspected of containing estradiol, a solid phase coupled to an antibody specific for estradiol, and a conjugate of the formula

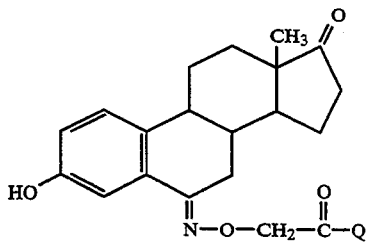

wherein Q is an enzyme, to form estradiol/antibody complexes and conjugate/antibody complexes on said solid phase;
b. separating said solid phase from said mixture;
c. measuring the amount of label present in said mixture or on said solid phase;
d. determining the amount of estradiol in said sample from the amount of label.

6. The method of claim 5 wherein said solid phase is a microparticle and said separation step comprises passing the mixture through a porous matrix.

7. In a method of determining the amount of estradiol in a fluid sample, the improvement comprising:
a. pretreating the sample by incubating the sample suspected of containing estradiol with 5α-dihydrotestosterone at a concentration within the range of about 1 μg/mL to about 5 μg/mL in a buffer at a pH within the range of from about 4.5 to about 6.7; and
b. measuring the amount of estradiol in the mixture.

8. The method of claim 7 wherein said buffer is a combination of glycine and citric acid.

9. A kit for performing an estradiol competitive enzyme immunoassay comprising:
a solid phase coupled to an antibody specific for estradiol;
a conjugate of the formula

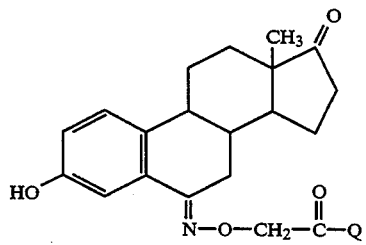

wherein Q is an enzyme; and
an enzyme substrate.

10. The kit of claim 9 wherein said enzyme is a peroxidase or phosphatase.

11. The kit of claim 9 further comprising a sample pretreatment solution comprising 5α-dihydrotestosterone at a concentration within the range of about 1 μg/mL to about 5 μg/mL.

* * * * *